United States Patent [19]

Terrell et al.

[11] 4,334,105

[45] Jun. 8, 1982

[54] METHOD FOR THE DEHALOGENATION OF ETHERS

[75] Inventors: Ross C. Terrell, Clark; Kirsten Hansen, Berkeley Heights, both of N.J.

[73] Assignee: Airco, Inc., Montvale, N.J.

[21] Appl. No.: 176,297

[22] Filed: Aug. 8, 1980

Related U.S. Application Data

[63] Continuation of Ser. No. 33,293, Apr. 25, 1979, abandoned.

[51] Int. Cl.$^3$ .................. C07C 41/24; C07C 41/44; C07C 41/18
[52] U.S. Cl. ............................. 568/682; 568/683; 568/684
[58] Field of Search .................. 568/682, 683, 684

[56] References Cited

U.S. PATENT DOCUMENTS 2,691,052 10/1954 Cines .................................. 568/682
3,391,204 7/1968 Young ................................ 570/156

*Primary Examiner*—Howard T. Mars
*Attorney, Agent, or Firm*—Roger M. Rathbun; Larry R. Cassett

[57] ABSTRACT

Methods for the dehalogenation of various haloethers are disclosed, comprising providing a haloether having the formula $CX'_3\text{-}[CY_2]_n\text{-}O\text{-}CZ_2\text{-}CX_3$ in which X', Y, Z and X are specifically disclosed combinations of hydrogen, fluorine chlorine and bromine such that the molecule includes at least one reducible group, but where both portions of any ethyl groups present are not reducible. Dehalogenation of these haloethers is carried out by contacting same with a hydrogen donor comprising an amine, preferably a primary or secondary amine or a primary, secondary or tertiary alkanol amine. The amine is preferably used in combination with a catalyst, such as a varivalent metal or a salt thereof, such as copper or a copper salt.

17 Claims, No Drawings

METHOD FOR THE DEHALOGENATION OF ETHERS

This is a continuation of application Ser. No. 33,293, filed Apr. 25, 1979, now abandoned.

FIELD OF THE INVENTION

The present invention relates to methods for dehalogenation of various haloethers. More specifically, the present invention relates to the use of amines to effect dehalogenation of certain specified halogenated ethers. Still more particularly, the present invention relates to methods for purification of certain haloethers by the dehalogenation of the undesired constituents thereof.

BACKGROUND OF THE INVENTION

The dehalogenation of certain halogenated alkanes utilizing various organic amines, either alone or in combination with catalysts, is well known. In particular, U.S. Pat. No. 3,391,204 to Young discloses methods for preparing halogenated hydrocarbons comprising such a process. In particular, the patentee teaches the dehalogenation of a halogeno-alkane having the following formula:

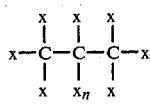

wherein the x's represent chlorine, bromine and fluorine atoms, and molecules containing up to four carbon atoms can be employed with certain combinations of these halogens thereon. Dehalogenation is carried out by contacting these molecules in the liquid phase with an amine having a $pK_a$ value above 5.2, preferably in the presence of a catalyst such as a metal-containing catalyst, including copper and copper salts.

In the past, various methods have been employed in order to produce desirable halogenated ethers. For example, U.S. Pat. No. 3,527,813 to Terrell, assigned to the assignee of the present application, discusses a method for the production of 1,1,2-trifluoro-2-chloroethyl difluoromethyl ether. In the commercial production of this compound. However, it is extremely difficult to produce that compound in a pure state, and a certain amount of 1,1,2-trifluoro-2,2 dichloroethyl difluoromethyl ether ($CHF_2OCF_2CFCl_2$) is generally produced therewith.

Improved processes for the purification of these halogenated ethers have therefore been sought.

SUMMARY OF THE INVENTION

In accordance with the present invention, it has now been discovered that certain specified haloethers can be dehalogenated by contacting these haloethers with a hydrogen donor, such as an amine, including the primary and secondary amines, and the primary, secondary and tertiary alkanol amines. More particularly, the haloethers which are dehalogenated in accordance with the present process have the following general formula (I):

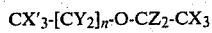

wherein n is 0 or 1, and in particular where the haloethers meet the following requirements:

(a) When n is 0, $CX'_3$ can be either $CH_3$ or $CF_2A$ (A being either hydrogen, fluorine, chlorine, or bromine), and $CZ_2$ can be either $CF_2$, $CFA'$ or $CA'_2$, A' being either chlorine or bromine, so that $A'_2$ is either $Cl_2$, $Br_2$ or ClBr. Where $CZ_2$ is $CF_2$, $CX_3$ can be either $CFA'_2$ or $CA'_3$ (A' again being either chlorine or bromine); when $CZ_2$ is $CFA'$, $CX_3$ is $CFA'_2$ (i.e., either $CFCl_2$, $CFBr_2$ or CFClBr): and when $CZ_2$ is $CA'_2$, $CX_3$ is $CF_3$. In connection with these methylethyl ethers, there is the added requirement that $CZ_2$ and $CX_3$ cannot both be reducible groups, but at least one of these two groups, $CZ_2$ and $CX_3$, must be reducible; and (b) When n is 1, $CZ_2$ and $CX_3$ are the same as in (a), and $CY_2$ and $CX'_3$ are either (1) the same as $CZ_2$ and $CX_3$, respectively, in (a) or (2) $CY_2$ can be $CF_2$, $CFA''$ (where A'' is hydrogen, chlorine or bromine), $CHA'$ or $CH_2$. In this case, where $CY_2$ is $CF_2$, $CX'_3$ is either $CF_3$, $CHFA'$, $CHA'_2$ or $CF_2A''$, where $CY_2$ is $CFA''$, $CX'_3$ is either $CF_3$ or $CF_2A'$, where $CY_2$ is $CHA'$, $CX'_3$ is $CF_3$, and where $CY_2$ is $CH_2$, $CX'_3$ is either $CF_3$, $CH_3$ or $CHF_2$.

In one embodiment of the present invention the amines acting as hydrogen donors can include the primary and secondary amines, and the primary, secondary and tertiary alkanol amines.

In a preferred embodiment of the present invention a methylethyl ether will be employed, that is where n is 0, preferably where $CX'_3$ is $CF_2H$ and $CZ_2$ is $CF_2$. Most preferably, $CX_3$ will then comprise $CFA'_2$, and in particular where A' is chlorine, i.e., $CFA'_2$ is $CFCl_2$. In that case the overall haloether employed will be $CF_2H$-O-$CF_2$-$CFCl_2$.

In another preferred embodiment of the present invention, where $CX'_3$ is $CF_2H$, $CZ_2$ will be $CA'_2$, preferably where A' is chlorine, so that $CZ_2$ will be $CCl_2$. As set forth above, in this case $CX_3$ will be $CF_3$, and the overall haloether employed will be $CHF_2$-O-$CCl_2$-$CF_3$.

In another embodiment of this invention, the dehalogenation is conducted in the presence of a catalyst, which preferably comprises a metal-containing catalyst such as a varivalent metal or a salt thereof. Most particularly, the metal or metal salt comprises copper, silver, cobalt, tin, manganese or nickel.

DETAILED DESCRIPTION

The process of the present invention principally involves bringing into reactive relationship, preferably in the liquid phase, a haloether of the type embraced by formula (I) above, and a hydrogen donor comprising an amine, in the dehalogenation reaction hereof. A number of primary, secondary and tertiary amines will be useful in the present invention, including the primary, secondary and tertiary alkanol amines, since they can act as hydrogen donors in the present method. In particular, alkyl amines, such as mono or dimethyl or diethyl amines, and alkanol amines such as mono, di or triethanol amines, are quite useful herein, as are the cyclic amines such as morpholine and piperadine, while the aromatic amines would not be useful herein.

The specific haloethers which can be employed in the process of the present invention have been set forth in formula (I) above. In understanding the mechanisms of the present invention, however, it would be helpful to appreciate that there are three principle reactions which halogenated ethers can undergo in the presence of various bases. The first of these is a hydrolysis or nucleophilic displacement reaction in which the halogen is replaced by a hydroxide or alkoxide or other nucleophilic group. The second of these reactions is dehydrohalogenation in which a hydrogen and halogen atom are removed from adjacent carbon atoms and a double bond is formed in their place. Both of these reactions must be avoided in accordance with the dehalogenation or reduction of the present invention. One can therefore establish certain guidelines in helping to understand the mechanisms by which the present dehalogenation reaction occurs. The first factor which must be understood is that in order for a compound to be "reducible" in accordance with the present invention there must either be two chlorine atoms, two bromine atoms or a chlorine and a bromine atom on one of the carbon atoms of that compound. On the other hand, referring again to formula (I), either in the case of $CZ_2$-$CX_3$ or $CY_2$-$CX'_3$ neither can have the configuration O-CH-CCl or O-CH-CBr, since the most likely reaction which would occur in connection with such a compound would be the elimination of HBr or HCl in accordance with the abovenoted dehydrohalogenation reaction, to produce O—C=C in the presence of a base. Two possible exceptions to this rule, however, are the compounds $CF_3OCHFCF_2Br$ and $CF_3OCHFCH_2Cl$.

Finally, another rule of thumb which can be followed in understanding these dehalogenation reactions is that in either the case of $CZ_2$-$CX_3$ or $CY_2$-$CX'_3$ should there be more than one hydrogen on the beta carbon (i.e., should Z include more than one hydrogen) unless $CY_2$ is $CH_2$ or $CF_2$ many of these compounds would not only be unstable to base but would spontaneously decompose.

The present invention is particularly useful and valuable for the purification of 1,1,2-trifluoro-2-chloroethyl difluoromethyl ether, primarily from a mixture of that compound with 1,1,2-trifluoro-2,2-dichloroethyl difluoromethyl ether.

The organic amines which can be used in accordance with the present process are discussed above. Specific examples of organic amines which will be useful in accordance with this process includes methyl amine, dimethyl amine, ethyl amine, diethyl amine, isopropyl amine, di-n-propyl amine, peperidine, morpholine, monoethanol amine, diethanol amine, triethanol amine etc.

In carrying out the process of the present invention, it is preferred that the molar ratios of the haloethers and the amine reactants employed, while variable within wide ranges, must be at least 1:1, i.e., that there must be at least one mole of amine present for each mole of haloether.

The temperature at which the process of the present invention is carried out will be dependent upon the particular reactants employed and may range, for example, from about 0° C. to about 100° to 120° C. or higher, and preferably from about 20° C. to about 80° C. The temperatures and/or pressures employed will of course be advantageously selected so that the reaction mass remains in a liquid state during the reaction itself. Furthermore, the time of reaction is not of great significance, and can be selected in accordance with the requirements of the particular process being conducted. In general, however, the time would depend upon the particular reactants employed, the reaction temperatures, whether or not a catalyst is employed, and other such factors. As for the pressures at which the process of the present invention is carried out, that will also be dependent primarily upon the particular reactants utilized, etc. Again, as noted above, the reaction pressure will preferably be chosen in order to maintain the reaction in the liquid phase. Preferably, of course, the reaction will be carried out at atmospheric pressure.

The present reaction may be effected in the presence of an at least substantially inert liquid solvent or diluent. The reaction medium can contain up to a few percent water, but the rate itself will then tend to be much slower. Since it is preferable to maintain the amine haloether, as well as any catalyst employed, in a single phase, the selection of miscible amine-haloether combinations will be preferred. In the case, however, where a miscible combination is employed it will be advantageous to provide an inert, liquid solvent or diluent therewith.

By an "inert" liquid is meant one which will not adversely affect the course of the reaction or the constitution of the reaction product. Specific examples of such inert liquid solvents or diluents which can be employed in accordance with the present invention are various alkanes, such as pentane, hexane, heptane, octane, nonane, etc., aromatic hydrocarbons such as benzene, toluene and xylene, cyclic ethers such as tetrahydrofuran, tetrahydro-2-methylfuran, m-dioxane, various aliphatic ethers such as dialkyl ethers, including diethyl ether and dipropyl ether, glycol monoethers such as glycol monomethylether, and various ketones, including acetone.

As discussed above, the present process will preferably be carried out in the presence of a catalyst for that reaction. The catalyst, in finely divided or other suitable state, may be a metal-containing (advantageously in most cases a varivalent metal-containing) catalyst, and more particularly a copper-containing catalyst such as a metallic (elementary) copper or a copper salt of an inorganic or organic acid, such as for example cuprous or cupric chloride, bromide, nitrate, acetate, propionate, etc., or the corresponding salts of silver, cobalt, tin, manganese, nickel, iron, molybdenum, chromium, antimony, vanadium and the like, or the said varivalent metals in elementary form or alloys thereof with each other or with other metals. It is preferred that a copper-containing catalyst, specifically elementary copper in powder form or a cuprous or cupric salt be employed. In general, use of a catalyst comprised of, for example, one or more of the aforesaid metals or of inorganic or organic salts thereof gives higher conversions, shortens induction periods, lowers operating temperatures, and provides a wider choice of useful amines.

The product produced in accordance with the dehalogenation process of the present invention may then be purified or isolated by means suitable therefore. This would ordinarily involve distillation or the like, and such processes will be apparent to those skilled in the art. In particular, product isolation in accordance with the disclosure of U.S. Pat. No. 3,391,204 from lines 25 through 50, at column 7 thereof, is referred to, and incorporated herein by reference thereto.

The present invention can be more fully understood in accordance with the following examples which are given by way of illustration only and not by way of limitation.

EXAMPLE 1

In order to purify $CHF_2OCF_2CHFCl$ from a mixture of that compound with $CHF_2OCF_2CFCl_2$ 95 grams of $CHF_2OCF_2CHFCl$ and 5 grams of $CHF_2OCF_2CFCl_2$ were refluxed with 24 grams of ethanol amine (HOCH$_2$CH$_2$NH$_2$) and 4 grams of copper powder for a period of 24 hours. The reaction mixture was then cooled and washed with water and dilute hydrochloric acid yielding a product which included 89 grams of CHF$_2$OCF$_2$CHFCl which contained less than 0.01% of the original CHF$_2$OCF$_2$CFCl$_2$.

EXAMPLE 2

In order to purify CF$_3$CHClOCHF$_2$ from a mixture of that compound with CF$_3$CCl$_2$OCHF$_2$ 95 grams of the CF$_3$CHClOCHF$_2$ and 5 grams of the CF$_3$CCl$_2$OCHF$_2$ were refluxed with 50 grams of triethanol amine (HOCH$_2$CH$_2$)$_3$N) and four grams of cupric chloride for a period of five hours. The reaction mixture was then cooled, washed with water and dilute hydrochloric acid yielding a product which contained 92 grams of the CF$_3$CHClOCHF$_2$ which contained less than 0.1% of the CF$_3$CCl$_2$OCHF$_2$.

It will also be understood that the haloethers which are produced in accordance with the present invention are useful as chemical intermediates, as anesthetics and for various other purposes.

What is claimed is:

1. A method for the dehalogenation of haloethers comprising providing a haloether having the formula:

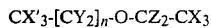

$$CX'_3\text{-}[CY_2]_n\text{-}O\text{-}CZ_2\text{-}CX_3$$

where n is 0 or 1, and wherein
    (a) when n is O, CX$'_3$ is selected from the group consisting of CH$_3$ and CF$_2$A, where A is selected from the group consisting of H, F, Cl and Br, CZ$_2$ is selected from the group consisting of CF$_2$, CFA$'$, and CA$'_2$, where A$'$ is selected from the group consisting of Cl and Br, provided that when CZ$_2$ is CF$_2$, CX$_3$ is selected from the group consisting of CFA$'_2$ and CA$'_3$, when CZ$_2$ is CFA$'$, CX$_3$ is CFA$'_2$, and when CZ$_2$ is CA$'_2$, CX$_3$ is CF$_3$; and provided that CZ$_2$ and CX$_3$ are not both reducible, but at least one of CZ$_2$ and CX$_3$ is reducible; and
    (b) when n is 1, CZ$_2$ and CX$_3$ are the same as in (a) and either (1) CY$_2$ and CX$'_3$ are the same as CZ$_2$ and CX$_3$, respectively, in (a) or (2) CY$_2$ is selected from the group consisting of CF$_2$, CFA$''$, CHA$'$ and CH$_2$ provided that when CY$_2$ is CF$_2$, CX$'_3$ is selected from the group consisting of CF$_3$, CHFA$'$, CHA$'_2$ and CF$_2$A$''$, A$''$ being selected from the group consisting of H, Cl and Br, when CY$_2$ is CFA$''$, CX$'_3$ is selected from the group consisting of CF$_3$ and CF$_2$A$'$, where CY$_2$ is CHA$'$, CX$'_3$ is CF$_3$ and when CY$_2$ is CH$_2$, CX$'_3$ is selected from the group consisting of CF$_3$, CH$_3$ and CHF$_2$, and contacting said haloether with a hydrogen donor comprising an amine selected from the group consisting of primary alkylamines, secondary alkyl amines, primary, secondary and tertiary alkanol amines.

2. The method of claim 1 wherein n is 0.

3. The method of claim 2 wherein CX$'_3$ comprises CF$_2$A.

4. The method of claim 3 wherein A is hydrogen.

5. The method of claims 2, 3 or 4 wherein CZ$_2$ is CF$_2$.

6. The method of claim 5 wherein CX$_3$ is CFA$'_2$.

7. The method of claim 6 wherein A$'$ is chlorine.

8. The method of claims 2, 3 or 4 wherein CZ$_2$ is CA$'_2$.

9. The method of claim 8 wherein A$'$ is chlorine.

10. The method of claim 1 wherein said contacting of said haloether with said hydrogen donor is conducted in the presence of a catalyst selected from the group consisting of copper, silver, cobalt, tin, manganese, nickel, iron, molybdenum, chromium, antimony, vanadium, the salts thereof, and mixtures thereof.

11. The method of claim 1 wherein the mole ratio of said hydrogen donor to said haloether is at least 1:1.

12. The method of claim 10 wherein said catalyst is elementary copper.

13. The method of claim 10 wherein said catalyst is a copper salt.

14. A method for the purification of 1,1,2-trifluoro-2-chloroethyl difluoromethyl ether which comprises contacting a mixture of said 1,1,2-trifluoro-2-chloroethyl difluoromethyl ether and 1,1,2-trifluoro-2,2-dichloroethyl difluoromethyl ether with a hydrogen donor comprising an amine selected from the group consisting of primary alkylamines, secondary alkyl amines, primary, secondary and tertiary alkanol amines.

15. The method of claim 14 wherein said contacting with said hydrogen donor is carried out in the presence of a catalyst selected from the group consisting of copper, silver, cobalt, tin, manganese, nickel, iron, molybdenum, chromium, antimony, vanadium, the salts thereof, and mixtures thereof.

16. The method of claim 1 wherein said hydrogen donor comprises an alkanol amine.

17. The method of claim 16 wherein said alkanol amine is selected from the group consisting of ethanol amine and triethanol amine.

* * * * *